(12) United States Patent
Stearns et al.

(10) Patent No.: US 8,084,000 B2
(45) Date of Patent: Dec. 27, 2011

(54) DOPANT DELIVERY SYSTEM FOR USE IN ION MOBILITY AND ION TRAP MOBILITY SPECTROMETRY

(75) Inventors: Stanley D. Stearns, Gig Harbor, WA (US); Santos Anthony Puente, Poulsbo, WA (US); John Michael Kelly, Poulsbo, WA (US); Brian David Russell, Poulsbo, WA (US)

(73) Assignee: VICI Metronics, Inc., Poulsbo, WA (US)

( * ) Notice: Subject to any disclaimer, the term of this patent is extended or adjusted under 35 U.S.C. 154(b) by 558 days.

(21) Appl. No.: 12/352,948

(22) Filed: Jan. 13, 2009

(65) Prior Publication Data

US 2009/0255351 A1    Oct. 15, 2009

Related U.S. Application Data

(60) Provisional application No. 61/043,936, filed on Apr. 10, 2008, provisional application No. 61/074,505, filed on Jun. 20, 2008, provisional application No. 61/079,059, filed on Jul. 8, 2008.

(51) Int. Cl.
*B01J 7/00*     (2006.01)
*B01D 46/00*    (2006.01)

(52) U.S. Cl. .......... 422/305; 55/503; 55/504; 73/864.81; 250/288; 96/105

(58) Field of Classification Search ................ None
See application file for complete search history.

(56) References Cited

U.S. PATENT DOCUMENTS

| | | | | |
|---|---|---|---|---|
| 4,132,186 | A | * | 1/1979 | Manske et al. ............... 116/216 |
| 4,522,713 | A | * | 6/1985 | Nussbaumer et al. ......... 210/136 |
| 5,041,094 | A | * | 8/1991 | Perego et al. ................. 604/143 |
| 5,270,219 | A | * | 12/1993 | DeCastro et al. ............. 436/180 |

* cited by examiner

*Primary Examiner* — Duane Smith
*Assistant Examiner* — Pankti Patel
(74) *Attorney, Agent, or Firm* — James E. Hudson, III; Crain, Caton & James, P.C.

(57) ABSTRACT

A device for introduction of an ammonia dopant into a spectrometry system without the use of a delivery system containing ammonia. The delivery device includes an ammonium solid that will, upon the introduction of heat, yield ammonia gas for delivery into the spectrometer system. Use of such an alternative to traditional ammonia dopant systems will yield little or no change in spectrometer readings. The volumetric flow rate of the ammonium is controlled by the use of capillary tubes as the exiting pathway, where the flowrate is determined by the cross sectional area and length of the capillary tube. Delivery of the ammonia is aided by use of a frit or screen to permit only gas to exit.

4 Claims, 2 Drawing Sheets

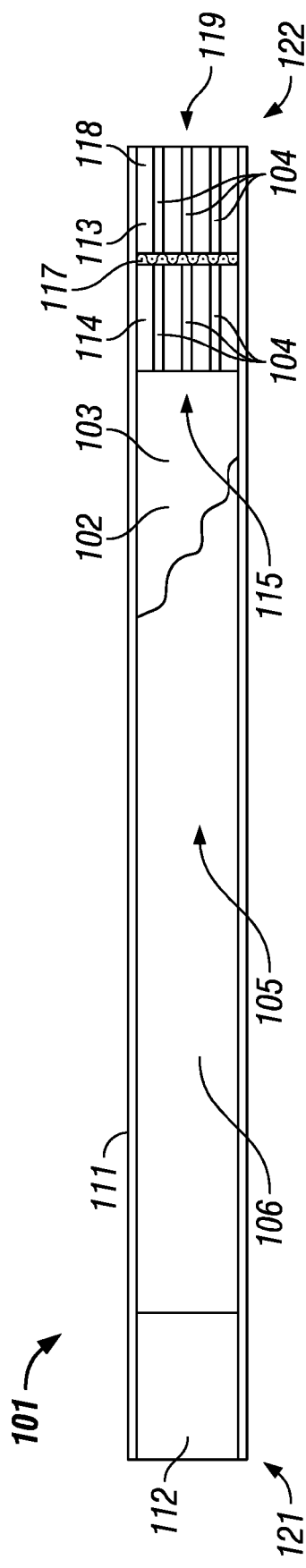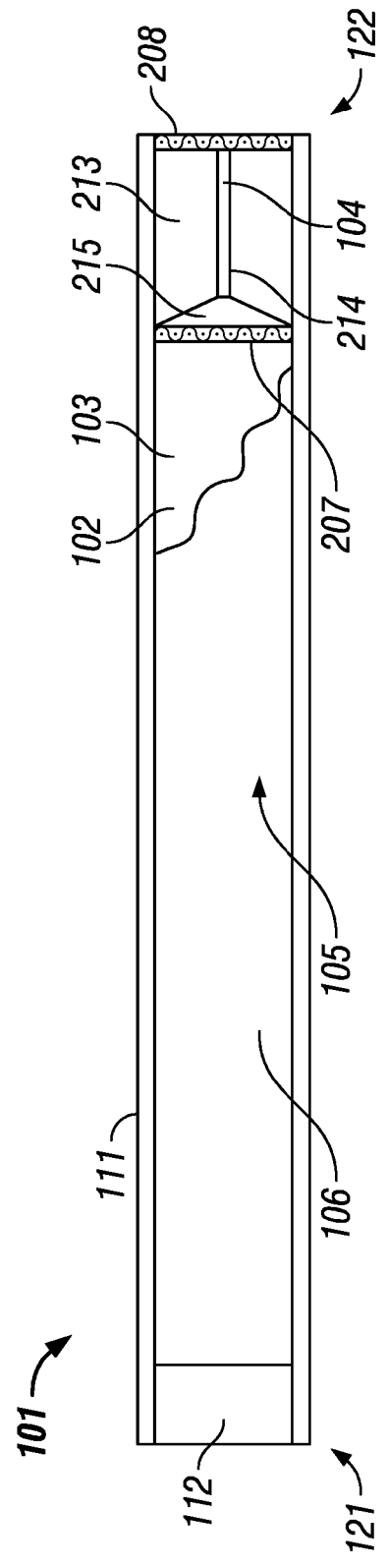

DOPANT DELIVERY SYSTEM FOR USE IN ION MOBILITY AND ION TRAP MOBILITY SPECTROMETRY

CROSS REFERENCE TO RELATED APPLICATIONS

This application claims the benefit of U.S. Provisional Patent Application No. 61/043,936 entitled, "Dopant Delivery System for Use in Ion Mobility and Ion Trap Mobility Spectrometry," filed on Apr. 10, 2008 in the United States Patent and Trademark Office and U.S. Provisional Patent Application No. 61/074,505 entitled "Improved dopant delivery system for use in ion mobility and ion trap mobility" filed on Jun. 20, 2008 in the United States Patent and Trademark Office and U.S. Provisional Patent Application No. 61/079,059 entitled "Dopant delivery system for use in ion mobility and ion trap mobility" filed on Jul. 8, 2008 in the United States Patent and Trademark Office.

STATEMENT REGARDING FEDERALLY SPONSORED RESEARCH OR DEVELOPMENT

Not Applicable.

BACKGROUND OF THE INVENTION

1. Field of the Invention

The present invention relates to an apparatus for delivery of an ammonia dopant into a spectrometry system, such as an ion mobility or ion trap mobility spectrometer. Such spectrometers are commonly used for detection of narcotics, explosives or chemical weapons by law enforcement or military officials. This invention further pertains to an apparatus for use in the delivery of an ammonia dopant into a spectrometer system in which the apparatus can be transported and stored without the inherent costs and difficulties associated with the transport, storage and use of pure ammonia.

2. Description of the Related Art

A typical spectrometer of the type in which the present invention is used is an ion mobility spectrometer (IMS) or an ion trap mobility spectrometer (ITMS) used for detection and identification of low concentrations of chemicals. The presence of such chemicals may be used to indicate the presence of narcotics, explosives or chemical weapons to law enforcement officials.

IMS and ITMS systems detect and identify low concentrations of chemicals by measuring the time it takes an ionized sample to traverse a homogeneous electric field within an enclosed tube.

In IMS and ITMS, sample vapor or particulate matter of interest is first collected in a sample trap. In ITMS systems, the sample is then filtered through a semi-permeable membrane to extract unwanted dust and dirt. Sample molecules are then transported on a stream of carrier gas into a chamber in which the sample is ionized by, for example, corona discharge, atmospheric pressure photoionization, electrospray ionization, or introduction of a radioactive source. The ionized sample is then introduced into an enclosed tube in which a homogeneous electric field is present (in IMS the ionized particles must traverse a gating mechanism which only allows particles of specific polarity into the enclosure, while in ITMS, the particles are allowed to reach equilibrium and then are guided to the enclosure). The electric field in the enclosure drives the ionized sample through neutral molecules present within the enclosure to the opposite end of the enclosure, where a detector, such as a Faraday plate or mass spectrometer, measures the arrival of ionized species. The time measured between introduction of a sample and its arrival at the detector is directly proportional to the size of the ion and thus can be used to identify the presence of specific ions.

Interference in, and thus reduced efficiency of, an IMS or ITMS system may be created by ionization and subsequent detection of carrier gases. However, introduction of a low-concentration of a dopant may be utilized to accept the transfer of charges created during ionization of the carrier gas. Such an introduction may give rise to constant detector readings, which can be utilized for proper system calibration and proper system output. The carrier gas may be doped by flowing around a permeation tube, where a controlled concentration of a first dopant is added to the air stream. The permeation tube may be temperature-controlled, the temperature preferably being maintained by a thermostat to insure a constant flow of the dopant. This temperature control may be application of heat to the permeation tube by a heating component of the spectrometer.

For example, an IMS or ITMS system being utilized for the detection of alkaloids, such as narcotics, would be run in positive mode. Running of an IMS or ITMS system in a positive mode indicates the introduction of positively charged molecules into the carrier gas and sample during ionization. Sensitivity of such a device is enhanced through the introduction of an abundance of protons during ionization to ionize a higher percent of the sample of interest. However, such an introduction may ionize the carrier gas and yield a vast abundance of extraneous readings, leading to enhanced sensitivity at the cost of reduced data value. The introduction of a dopant charge transfer mediator with a proton affinity would serve to allow transfer of the positive charge to the dopant instead of the carrier gas, avoiding the ionization of the carrier gas. Thus, a single reading indicating the presence of the dopant is outputted with the continued increase in instrument sensitivity.

In searching for narcotics, spectrometers commonly are setup to detect alkaloids. In order to ensure the continued creation of a positive charge within alkaloids present in a sample, and to ensure the continued relative neutrality of carrier gas, it is important to select a dopant with a proton affinity lower than the narcotic, yet higher than the carrier gas. Ammonia's proton affinity is between that of common carrier gases, such as air or nitrogen, and that of alkaloids. It is common knowledge within the industry that ammonia suits these characteristics, and thus ammonia is the primary dopant used for detection of narcotics within an IMS or ITMS system.

The use of ammonia, however, creates a number of difficulties. Ammonia is a pressurized liquid at room temperature. When provided as a liquid, transportation is strictly controlled. Therefore, liquefied ammonia has typically been sealed in a permeation tube, and frozen until use. When used the permeation tube permits the controlled introduction of the dopant into a gaseous stream after permeation though a membrane between concentrated dopant and the gaseous stream. Ensuring a continuous flow rate from the permeation tube is sometimes problematic. Thus permeation tube construction can exacerbate these problems. IMS or ITMS systems commonly introduce the dopant into the system via introduction of the dopant into the carrier gas upstream from introduction of the sample. These limitations result in the permeation tube size being limited to 0.5 cubic centimeters, which typically limits the ammonia product's lifespan to six-weeks. As a further difficulty, ammonia is also very alkaline and reacts corrosively with all body tissues. Thus, additional safety measures must be abided by during transport of ammonia. In light of such difficulties, the use of ammonia as a dopant within a narcotic-detecting IMS or ITMS system is difficult.

SUMMARY OF THE INVENTION

It is therefore, a principle object of the present invention to provide a delivery system of ammonia for use as a dopant in a spectrometry system without the difficulties found in a traditional ammonia dopant system and without reduction in spectrometer response.

It is a further object of the present invention to provide a delivery system to introduce ammonia into a spectrometry system though the introduction of temperature above room temperature in or about the delivery system and to do so at a constant flow rate.

It is an advantage of the present invention to obtain proper spectrometer system calibration and proper spectrometer system output through the use of an ammonia dopant without the drawbacks, such as storage, transport and lifespan concerns, associated with the use, transport and storage of an ammonia delivery system, such as an ammonia diffusion or permeation tube. It is a further advantage to provide a delivery system capable of introducing ammonia into a spectrometry system without being subjected to limitations on the size and methods of ammonia transport when shipping such delivery systems.

The foregoing advantages are achieved through the implementation of an ammonia supply system, where the ammonia originates in a solid ammonium form and which is released after heat is applied. The released ammonia is then transported from the reservoir that houses the system and is released at a constant rate by virtue of the construction of the permeation tube. The side-product of the thermally-induced reaction, carbon dioxide, is also delivered into the spectrometer.

Such an ammonia dopant system could be implemented into most commercially produced IMS or ITMS systems though either a "drop-in" ammonia supply system or addition of such an ammonia supply system into an IMS or ITMS system's carrier gas provision system. Inclusion of such an ammonia supply system would increase system function without incurring costs associated with traditional pure ammonia dopant schemes.

Uses of IMS or ITMS systems commonly include detection of biological materials, chemical weapons, narcotics and explosives. Such uses by airport, postal and military personnel require continuous use of such systems. The use of the current invention allows for the improvement in IMS or ITMS system response though the use of ammonia doping without both the additional costs of ammonia shipping and the requirement of constantly replacing a traditional unit that may only have a 6-week lifespan.

The foregoing and other objectives, features and advantages of the invention will be more readily understood upon consideration of the following detailed description of the invention, taken in conjunction with the accompanying drawings.

BRIEF DESCRIPTION OF THE DRAWINGS

So that the manner in which the described features, advantages and objects of the invention, as well as others which will become apparent, are attained and can be understood in detail, more particular description of the invention briefly summarized above may be had by reference to the embodiments thereof that are illustrated in the drawings, which drawings form a part of this specification. It is to be noted, however, that the appended drawings illustrate only a typical preferred embodiment of the invention and are therefore not to be considered limiting of its scope as the invention may admit to other equally effective embodiments.

FIG. 1 illustrates an ammonium supply system of the present invention.

FIG. 2 illustrates an alternative ammonium supply system.

DETAILED DESCRIPTION OF THE PREFERRED EMBODIMENT

Figure 3:
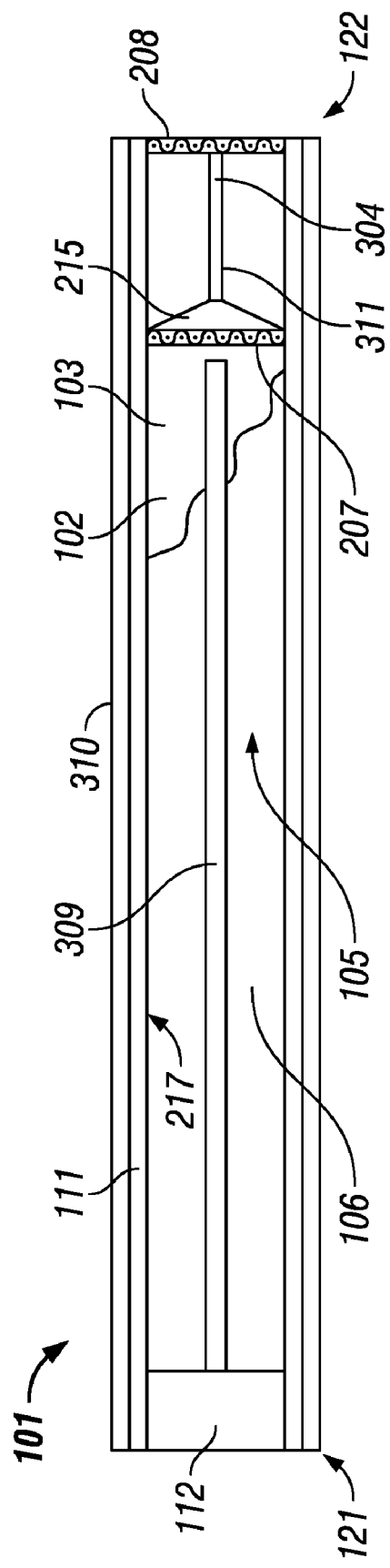
FIG. 3 illustrates another alternative ammonium supply system.

The present invention involves an improvement to the dopant delivery system in a chemical detection device such as a spectrometer, for example an ion mobility or ion trap mobility spectrometer. Generally, a typical IMS or ITMS spectrometer includes one or more devices to introduce a dopant to serve as a charge transfer mediator. Such an introduction device may be, and commonly is, attached such that dopant is delivered into the carrier gas prior to introduction of the sample. In a preferred embodiment, an ammonia dopant is delivered into a spectrometry system though a delivery system that derives the distributed ammonia from ammonium carbamate, with no or no significant reduction in spectrometer response.

Referring to FIG. 1, in the preferred embodiment of the ammonia gas delivery apparatus invention 101, ammonia gas 102, along with carbon dioxide gas 103, is provided for introduction into the carrier gas stream via sets of chemically-inert capillary tubes 104 communicating with a reservoir 105 of a solid ammonia-releasing compound 106, preferably ammonium carbamate, $NH_2COONH_4$, although ammonium carbonate, $(NH_4)_2CO_3$ or other ammonia releasing compounds may be used.

Use of a solid ammonia-releasing compound 106 provides several advantages, among them that it may be stored as a solid. Thus, a reservoir 105 containing solid ammonia-releasing compound 106 may be utilized in shipping and operation, providing improved safety and compact storage. Moreover, because it is known that such compounds begin to decompose above 35° C. and completely decompose to ammonia, $NH_3$ and carbon dioxide, $CO_2$ above 60° C., the rate of production of ammonia and carbon dioxide may be controlled by the application of heat to the solid ammonia-releasing compound 106. Problematically, while such compounds are typically anhydrous, they tend to draw water from the surrounding air, and thus produce water as a byproduct. Ammonium carbamate is preferred for its stability compared to other ammonia-releasing compounds, its consistent ammonia release at sublimation and its comparatively lower carbon dioxide release.

The thermal driving force required to release the ammonia gas 102 may be introduced in any of several ways commonly known within the industry. In the preferred embodiment, the container is sized to match the permeation tube receptacle where heat is applied by the spectrometer assembly to a permeation tube and thus the reservoir 105 be heated By providing a reservoir 105, the solid ammonia-releasing compound 106, preferably ammonium carbamate, may be generally isolated from the atmosphere. Isolation from atmosphere is particularly important as solid ammonia-releasing compound 106, such as ammonium carbamate, are very hygroscopic, drawing water from the atmosphere by absorption and by adsorption. Moreover, enclosing the reservoir 105 retards potential decomposition by avoiding the transfer of heat from ambient air. In the preferred embodiment, the reservoir 105 is composed of a chemically-inert materials.

The reservoir 105 may be constructed from a hollow tube 111, preferably of a chemically-inert material, preferably PTFE, with a solid, preferably chemically-inert, end plug 112 at or proximate the first end 121 of hollow tube 111 and a multiple-component plug 113 at or proximate the second end 122 of hollow tube 111. Alternatively, the reservoir 105 may be constructed from a hollow tube 111 with multiple-component plugs 113 at each end. The construction of the multiple-component plug 113 reduces the potential that material can escape and enhances the constancy of the gaseous flow rate from the invention 101. Multiple-component 113 includes a first plug 114, a first set 115 of a plurality of capillary tubes 104, a frit or screen 117, preferably a course metal frit, a second plug 118 and a second set 119 of a plurality of capillary tubes 104. The frit 117 contains a like number of passages to the number of capillary tubes in each set 115, 119 and are aligned to provide a passage from the reservoir 105. In the preferred embodiment, the first set 115 and the second set 119 of capillary tubes 104 each contain three (3) capillary tubes 104 with each set of equal interior total cross-sectional area. However first set 115 of capillary tubes 104 may have a different total interior cross-sectional area to provide a particular flow rate from reservoir 105. Each set 115, 119 of capillary tubes 104 is maintained in placed by an associated plug 114, 118, through which each capillary tube 104 is positioned. The multiple-component plug 113 may fit to the hollow tube 111 with a press fit or by forming the plug 114, 118 about a set 115, 119 of capillary tubes 104 or by other means known in the art. Of importance is that there be no passage between capillary tube 116 and a plug 114, 118 to permit communication between the reservoir 105 and the outside of invention 101 as any passage would alter the combined cross-sectional area for ammonia dispersion and therefore the flow rate from invention 101.

The use of a plurality of capillary tubes 104 provides a constant and controlled flow rate as the passage of each capillary tube 104 provides a cross sectional area limiting the volume of gas exiting per unit time as the small cross sectional area and length of the capillary tube 104 restrict the flow rate. The capillary tube 104 simultaneously promotes flow from the container to the carrier gas by capillary action and limits the exiting flow rate to that which may pass through the capillary tube 104. In the preferred embodiment, the capillary tube 104 is composed of a chemically-inert material. Preferably, the capillary tube 104 is composed of polyetheretherketone (PEEK).

In operation, as heat is applied to or absorbed by the solid ammonia-releasing compound 106, it decays into carbon ammonia gas 102 and carbon dioxide gas 103. The ammonia gas 102 and carbon dioxide gas 103 then travel through each capillary tube 104 to be combined with the carrier gas of the spectrometry system. Thus, a controlled introduction of carbon dioxide 103 must be considered in calibrating the spectrometry system, thus still yielding precise and accurate results. The additional byproduct, water, is retained within the reservoir 105.

In an alternative embodiment illustrated in FIG. 2, a second plug 213 having a second plug passage 214 therethrough, may be inserted in the second end of the hollow tube 111. The capillary tube 104 may be positioned through the second plug passage 214. Thus, reservoir 105 may be defined by end plug 112, second plug 213, and hollow tube 111.

This alternative embodiment may further include in hollow tube 111, on the inner side of the capillary tube 104, a coarse frit or screen 207, preferably of metal, to prevent solid particles of solid ammonia-releasing compound 106 from passing into or out of the capillary tube 104. This frit or screen 207 may be constructed of a chemically-inert material, such as stainless steel. A second frit or screen 208, preferably of metal, may be positioned adjacent the capillary tube 104 at hollow tube second end 122. The frit or screens 207, 208 may be open pore frits.

Intermediate the capillary tube 104 and the frit or screen 207, a funnel 215, with an outer edge, may be provided in hollow tube 111 and which preferably is in continuous contact with the inner surface 217 of hollow tube 111 at the funnel's outer edge. The funnel 215 has an opening at its apex adjacent the frit or screen 207, where the opening is aligned with and equivalent to cross sectional area of the opening of the frit or screen 207 and that of the capillary tube 104. The funnel 215 preferably is adjacent the capillary tube 104 and the first screen 207. This combination of frit or screen 207, funnel 215 and capillary tube 104 is necessary for effective operation in this alternative embodiment. Each frit or screen 207 varies in structure and porosity. Therefore, it is necessary to utilize a capillary tube 104 to control the volumetric flow rate of the ammonia exiting the invention 101, which may be accomplished by selection of the length and cross-sectional area of the capillary tube 104. A funnel 215 is necessary to ensure that the ammonia released travels to and exits at capillary tube 104.

In another alternative embodiment, depicted in FIG. 3, solid ammonia-releasing compound 106 can be heated, electrically or chemically, with an interior heating element 309 within the reservoir 105 or by an exterior heating element 310. Additionally, the reservoir 105 may be constructed of a hollow tube 111 with an end plug 112 at its first end and a single capillary tube 304 at its second end. The capillary tube 304 may have a capillary tube wall 311 with an outer edge sufficiently close to the inner surface 217 of the hollow tube 111 to provide a press fit or may be sealed to the hollow tube 111. Thus, the thick capillary tube 304 provides both the plug and the capillary passage for gas delivery.

In one embodiment, the invention is implemented in a spectrometer system used to detect illicit narcotics. Such a system may, for example, be setup to detect alkaloids, which may indicate the presents of such narcotics.

In another embodiment, a spectrometer is setup to detect the presence of narcotic vapors through the detection of alkaloids. Such a device is commonly run in positive ion mode such that the introduction of positive ions would ionize the sample in order for the spectrometer to function properly. In order to allow the introduction of an abundance of positively charged particles without the ionization of the carrier gas, ammonia is commonly used as a dopant to accept the charged particles in the absence of a sample with a higher proton affinity, such as alkaloids.

Various alternatives and/or modifications may be made to the disclosed embodiments without departing from the spirit or scope of the invention.

The invention claimed is:

1. An ammonia gas delivery apparatus comprising:
   a hollow tube, said hollow tube having a hollow tube first end and a hollow tube second end;
   an end plug proximate said hollow tube first end;
   a multiple component plug proximate said hollow tube second end;
      said multiple-component plug comprising
         a first plug,
         a second plug,
         a metal frit having a plurality of passages therethrough adjacently intermediate said first plug and a second plug, a first set of a plurality of capillary tubes through said first plug, and a second set of a plurality of capillary tubes through said second plug;

a reservoir defined by said hollow tube, said end plug and said multiple component plug, said reservoir containing a solid ammonia-releasing compound.

2. The apparatus of claim 1, wherein said first set of capillary tubes and said second set of capillary tubes have an equal interior cross-sectional area.

3. The apparatus of claim 1, wherein said solid ammonia-releasing compound is ammonium carbamate.

4. An ammonia gas delivery apparatus comprising:

a hollow tube, said hollow tube having an end;

a multiple component plug proximate said hollow tube end;

said multiple-component plug comprising
a first plug,
a second plug,
a metal frit having a plurality of passages therethrough adjacently intermediate said first plug and a second plug,
a first set of a plurality of capillary tubes through said first plug, and
a second set of a plurality of capillary tubes through said second plug;

a reservoir within said hollow tube containing a solid ammonia-releasing compound.

* * * * *